(12) United States Patent
Goodin et al.

(10) Patent No.: US 7,763,043 B2
(45) Date of Patent: Jul. 27, 2010

(54) DILATATION CATHETER WITH ENHANCED DISTAL END FOR CROSSING OCCLUDED LESIONS

(75) Inventors: Richard Goodin, Blaine, MN (US); Robert E. Burgmeier, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1480 days.

(21) Appl. No.: 10/340,406

(22) Filed: Jan. 9, 2003

(65) Prior Publication Data

US 2004/0138691 A1 Jul. 15, 2004

(51) Int. Cl.
*A61M 29/00* (2006.01)
*A61D 1/02* (2006.01)

(52) U.S. Cl. ...................... 606/194; 606/159

(58) Field of Classification Search .............. 606/194, 606/159, 103.12, 104, 103.08, 103.07; 604/103.12, 604/104, 103.08, 103.07
See application file for complete search history.

(56) References Cited

U.S. PATENT DOCUMENTS

| | | | |
|---|---|---|---|
| 4,154,244 A | 5/1979 | Becker et al. | |
| 4,906,244 A | 3/1990 | Pinchuk et al. | |
| 5,108,415 A | 4/1992 | Pinchuk et al. | |
| 5,195,969 A | 3/1993 | Wang et al. | |
| 5,264,260 A | 11/1993 | Saab | |
| 5,306,246 A | 4/1994 | Sahatjian | |
| 5,328,468 A | 7/1994 | Kaneko et al. | |
| 5,358,486 A | 10/1994 | Saab | |
| 5,447,497 A | 9/1995 | Sogard et al. | |
| 5,512,051 A | 4/1996 | Wang et al. | |
| 5,697,944 A * | 12/1997 | Lary | 606/159 |
| 5,713,854 A | 2/1998 | Inderbitzen et al. | |
| 5,807,327 A | 9/1998 | Green et al. | |
| 6,500,148 B1 | 12/2002 | Pinchuk et al. | |
| 6,758,848 B2 * | 7/2004 | Burbank et al. | 606/45 |
| 6,951,566 B2 * | 10/2005 | Lary | 606/159 |

* cited by examiner

*Primary Examiner*—Darwin P Erezo
*Assistant Examiner*—Melissa Ryckman
(74) *Attorney, Agent, or Firm*—Vidas, Arrett & Steinkraus P.A.

(57) ABSTRACT

A catheter for crossing an occluding lesion with an inflatable balloon and dilating the lesion includes an inner tube that defines a longitudinal axis. The balloon includes a distal section that is bonded to the tube's distal end, a working section, and a conically shaped distal transition section connecting the working and distal section. A plurality of rigid ribs are spaced around the circumference of the balloon near the catheter's distal end. Each rib includes a first elongated portion attached to the balloon's distal section and aligned substantially parallel with the longitudinal axis. A second portion extending from the first portion and at an angle thereto is attached to and lies along the surface of the balloon's distal transition section. The plurality of ribs combine to simulate a stiff, tapered surface that can be wedged into the occluding lesion to create a passageway to cross the lesion with the balloon.

6 Claims, 3 Drawing Sheets

DILATATION CATHETER WITH ENHANCED DISTAL END FOR CROSSING OCCLUDED LESIONS

FIELD OF THE INVENTION

The present invention relates generally to surgical instruments. More particularly, the present invention pertains to transluminal dilatation catheters for revascularization of an occluded conduit or connective duct. The present invention is particularly, though not exclusively, useful for crossing an occluding lesion in a vascular conduit with a dilatation balloon and subsequently dilating the lesion to restore blood flow through the conduit.

BACKGROUND OF THE INVENTION

In coronary artery disease, the coronary arteries become narrow or blocked due to a gradual build-up of atherosclerotic plaque that affixes to the inner surface of the arterial wall. These lesions restrict the flow of blood through the diseased artery, and, if left untreated can result in complications that include acute myocardial infarction. The first percutaneous transluminal coronary angioplasty (PTCA) was performed in 1977, and has become a common medical intervention to revascularize diseased arteries. In a typical PTCA procedure, a small dilatation balloon is positioned across a targeted lesion and inflated to increase the luminal diameter of the affected artery. Most of the improvement in luminal diameter following balloon angioplasty results from the stretching of the arterial wall by the balloon, however plaque compression, splitting and axially redistribution can also contribute to an increase in luminal diameter.

In a typical PTCA procedure, the diseased coronary artery is accessed from a peripheral artery such as the femoral and brachial arteries. From the peripheral artery, the distal end of the catheter must navigate through the curves and bends of a tortuous vascular tree to reach a targeted lesion in an affected artery. Typically, a guidewire is used to establish a mechanical pathway to the site of the lesion, allowing the catheter to track the guidewire from the peripheral artery to the targeted lesion. To successfully track the guidewire through the tortuous vasculature, a catheter having a relatively flexible distal portion is required. On the other hand, a rather stiff proximal portion is generally prescribed to provide the pushability needed to advance the catheter along the guidewire.

A traditional limitation of PTCA is the treatment of totally occluded arteries. As indicated above, the PTCA protocol requires the positioning of a dilatation balloon across the lesion and thus a passageway through the lesion is required. Conventional catheters designed with flexible distal portions for trackability lack the necessary stiffness to advance through an occluding lesion, and thus have been generally limited to the treatment of partially blocked arteries.

SUMMARY OF THE INVENTION

The present invention is directed to a catheter for penetrating and dilating an occluding lesion within a vascular conduit of a patient. More specifically, the present invention is directed to a catheter having the ability to cross an occluding lesion and place a dilatation balloon into position to dilate the lesion. Structurally, the catheter includes a cylindrically shaped inner tube that extends from a distal end to a proximal end and defines a longitudinal axis. The inner tube is formed to surround an inflation lumen and a guidewire lumen, both of which pass between the inner tube's distal and proximal ends.

An inflatable balloon is mounted onto the inner tube at the distal end of the tube. For the present invention, the balloon extends from a balloon distal end to a balloon proximal end and generally includes five distinguishable sections therebetween. Starting at the distal end of the balloon, the balloon includes a distal section that is substantially cylindrical shaped and is sized to conform to the outer surface of the inner tube, allowing the distal section to be bonded to the inner tube. Proximal to this distal section, the balloon includes a distal transition section that is generally shaped as a truncated cone having a proximally increasing diameter. Continuing in the proximal direction, the balloon includes a working section that is provided to contact the lesion during dilation. Suitable shapes for the working section can include but are not limited to cylindrical and conical (i.e. a truncated cone having a proximally increasing diameter). The balloon further includes a cylindrical proximal section for bonding to the inner tube and a proximal transition section connecting the proximal transition section to the working section.

The balloon is attached to the inner tube to establish fluid communication between the balloon and the inflation lumen of the inner tube. With this cooperation of structure, an inflation fluid can be introduced into the proximal end of the inner tube at an extracorporeal location for delivery into the balloon. Pressurization of the balloon by the inflation fluid moves the balloon from the deflated configuration wherein the working section lies along the outer surface of the inner tube to an inflated configuration wherein the working section is radially distanced from the inner tube. Once inflated, the balloon can be deflated by drawing inflation fluid from the proximal end of the inner tube.

For the present invention, the distal end of the catheter includes a dilatation unit having a plurality of relatively short, spaced-apart ribs that combine to simulate a stiff, tapered surface that can be wedged into an occluding lesion to create a passageway through the lesion. The passageway can then be used to cross the lesion with the inflatable balloon. In greater structural detail, each rib includes a first elongated portion and a second elongated portion extending from the first portion and at an angle, $\alpha$, thereto. The first portion of the rib is attached to the cylindrical distal section of the balloon and aligned to be substantially parallel with the longitudinal axis. The second portion of the rib is attached to and lies along the surface of the conically shaped distal transition section of the balloon. In this manner, the plurality of stiffening ribs (typically 8-10 ribs) are attached to the balloon and evenly spaced around the circumference of the balloon.

As indicated above, the spaced-apart ribs combine to simulate a stiff, tapered surface that is established regardless of whether the balloon is inflated or deflated. In greater detail, each rib is made of a rigid material such as Liquid Crystal Polymer, Polyphenylene Sulfide or Polyethylene Naphthalate (PEN) or other applicable polymers or materials. When attached to the balloon, the distal end of each rigid rib is radially distanced from the longitudinal axis at a distance $d_1$ that is only slightly larger than the diameter of the inner tube. On the other hand, due to the angle, $\alpha$, between rib portions, the proximal end of each rigid rib is radially distanced from the longitudinal axis at a distance $d_2$, with $d_2 > d_1$. This cooperation of structure creates the simulated tapered surface that can be wedged into an occluding lesion to create a passageway.

In operation, a peripheral artery, such as the femoral artery is first pierced to provide access to the vascular tree and a sheath is positioned within the artery. Next, a guidewire is inserted into the peripheral artery, navigated through the vasculature and poked through the targeted occluding lesion.

With the guidewire in place, the dilatation balloon is deflated and the distal end of the catheter is threaded onto the guidewire. Next, the distal end of the catheter is inserted into the peripheral artery and pushed through the vasculature with the distal end of the catheter tracking the guidewire until the ribs contact the targeted occluding lesion. Next, the catheter is axially advanced to wedge the simulated tapered surface created by the ribs into the lesion and establish a passageway through the lesion surrounding the guidewire. If desired, the distal end of the catheter can be axially reciprocated back and forth to drive the ribs into the lesion and create the required passageway. Alternatively, the balloon can be partially inflated to assist in the creation of the passageway.

Once the lesion has been crossed, the working section of the balloon can be positioned to dilate the lesion. With the working section of the balloon positioned across the lesion, the balloon can be distended to dilate the lesion and restore blood flow to the affected vascular conduit. After the lesion has been dilated, the balloon can be deflated to thereby allow the catheter to be moved for treatment of another lesion or withdrawn from the patient's body.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
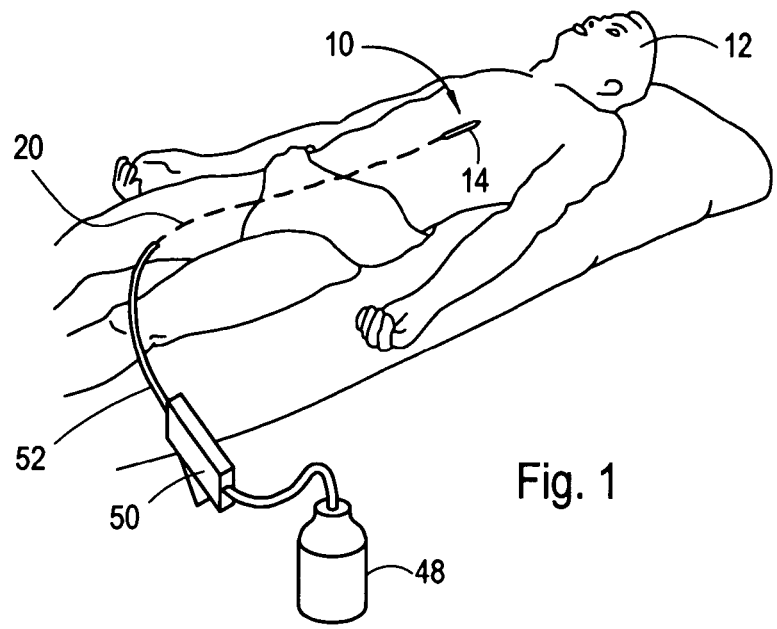
FIG. 1 is a simplified, schematic view showing an apparatus in accordance with the present invention operationally positioned in a patient to dilate a lesion in an upper body artery.

Referring initially to FIG. 1, a catheter for crossing an occluding lesion and dilating the lesion within a vascular conduit is shown and generally designated 10. More specifically, the catheter 10 is shown positioned for treatment of an upper body artery in a patient 12. Although the catheter 10 is capable of treating a lesion in an upper body artery such as a coronary artery, those skilled in the pertinent art will recognize that the use of the catheter 10 is not limited to upper body arteries, but, instead can be used in vascular conduits and other ductal systems throughout the human body.

Figure 2:
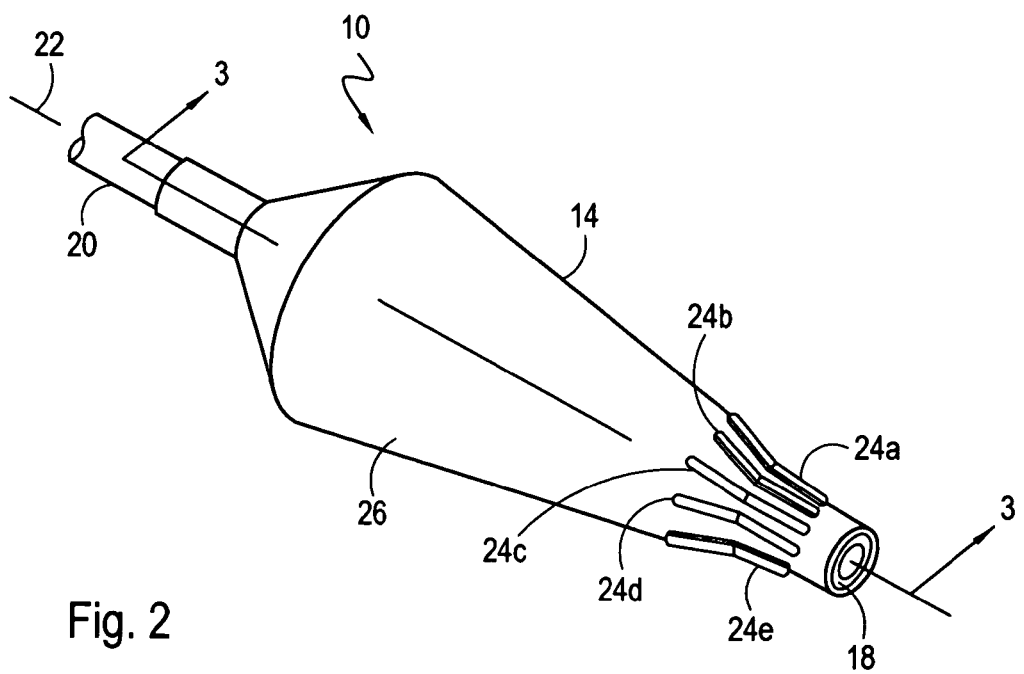
FIG. 2 is an enlarged perspective view of the distal portion of a catheter in accordance with the present invention, shown after balloon inflation.

Referring now to FIG. 2, the distal portion of the catheter 10 is shown to include an inflatable dilatation balloon 14 that is attached to the distal end 18 of an inner tube 20. Cross-referencing FIGS. 1 and 2, it can be seen that the inner tube 20 is elongated and defines a longitudinal axis 22 in the direction of elongation. It can be further seen that the length of the inner tube 20 is sized to allow the inner tube 20 to extend from an access point (e.g. the femoral artery) to the diseased vascular conduit (e.g. a coronary artery). As further shown in FIG. 2, the catheter 10 includes a dilatation unit having a plurality of ribs 24, of which ribs 24a-e are shown, that are attached to the external surface 26 of the balloon 14 and circumferentially distributed around the balloon 14.

Figure 3:
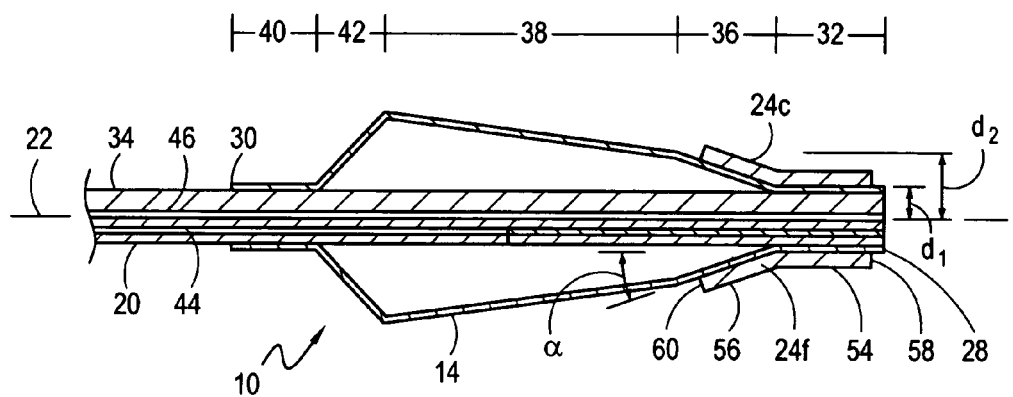
FIG. 3 is a sectional view of the catheter shown in FIG. 2 as seen along line 3-3 in FIG. 2.

As best seen in FIG. 3, the balloon 14 extends axially from a distal end 28 to a proximal end 30 and generally includes five distinguishable sections therebetween. Starting at the distal end 28 of the balloon 14, the balloon 14 includes a distal section 32 that is substantially cylindrical shaped and is sized to conform to the cylindrical outer surface 34 of the inner tube 20, allowing the distal section 32 to be bonded to the inner tube 20. Proximal to distal section 32, the balloon 14 includes a distal transition section 36 that is generally shaped as a truncated cone that narrows in the distal direction toward the distal end 28 of the balloon 14. The balloon 14 further includes a working section 38 that is provided to contact the lesion during dilation. As shown, the working section 38 can be shaped as a truncated cone that narrows in the distal direction toward the distal end 28 of the balloon 14. Alternatively, if desired, the working section can be cylindrically shaped (not shown). As further shown in FIG. 3, the balloon 14 includes a cylindrical proximal section 40 for bonding to the inner tube 20 and a proximal transition section 42 connecting the proximal transition section 42 to the working section 38.

With continued reference to FIG. 3, it can be seen that the inner tube 20 is formed with an inflation lumen 44 and a guidewire lumen 46. It can be further seen that the balloon 14 is attached to the inner tube 20 to establish fluid communication between the balloon 14 and the inflation lumen 44 of the inner tube 20. Cross referencing FIGS. 1 and 3, it is to be appreciated that an inflation fluid from fluid source 48 can be introduced into the inflation lumen 44 under control of controller 50 at the proximal end 52 of the inner tube 20 to pressurize the balloon 14. Pressurization of the balloon 14 by the inflation fluid moves the balloon 14 from the deflated configuration (shown in FIG. 4) wherein the working section 38 lies along the outer surface 34 of the inner tube 20, to an inflated configuration (shown in FIG. 3) wherein the working section 38 is radially distanced from the inner tube 20. Once inflated, the balloon 14 can be deflated by drawing inflation fluid from the balloon 14.

Continuing with reference to FIG. 3, it can be seen that each rib 24, such as rib 24f, includes an elongated first portion 54 and an elongated second portion 56 extending from the first portion 54 and at an angle, $\alpha$, thereto. Typically, the angle, $\alpha$, varies between approximately fifteen to forty-five degrees (15°-45°), but is not limited to this range. As further shown, the first portion 54 is attached to the cylindrical distal section 32 of the balloon 14 and aligned to be substantially parallel with the longitudinal axis 22. Also, the second portion 56 is attached to and lies along the surface of the conically shaped distal transition section 36 of the balloon 14. With this cooperation of structure, the distal end 58 of each rib 24 is radially distanced from the longitudinal axis 22 by a distance $d_1$ and the proximal end 60 of each rib 24 is radially distanced from the longitudinal axis by a distance $d_2$ with $d_2 > d_1$.

Suitable materials for the ribs 24 include but are not limited to Liquid Crystal Polymer, Polyphenylene Sulfide and Polyethylene Naphthalate (PEN) or other applicable polymers or materials. Suitable manufacturing methods for attaching each rib 24 to the balloon 14 include, but are not limited to heat bonding, bonding using a suitable adhesive, and extrusion of the ribs onto a balloon preform using an intermittent extrusion head followed by conventional balloon blowing techniques.

OPERATION

Figure 4:
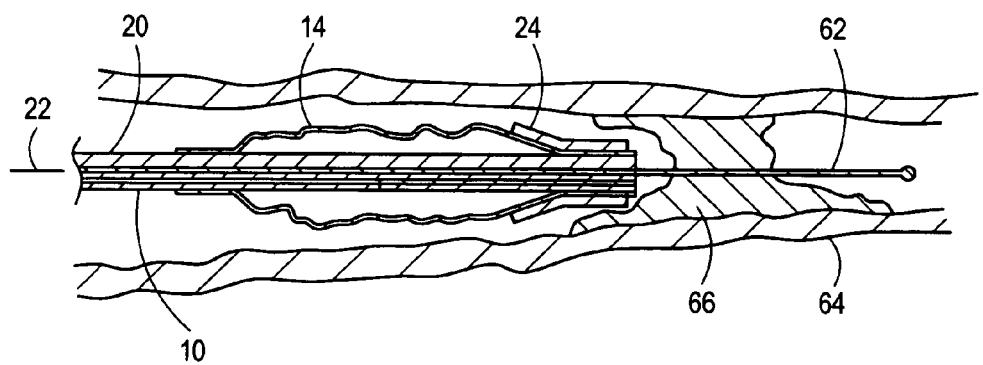
FIG. 4 is a sectional view of the distal portion of the catheter as in FIG. 3 shown positioned in a vascular conduit in front of an occluding lesion.

To use the catheter 10 of the present invention, access to the vasculature is obtained by piercing an opening in a peripheral artery, such as the femoral artery (see FIG. 1) and a sheath is positioned within the artery. Next, a guidewire, such as guidewire 62 shown in FIG. 4, is inserted into the opening and advanced through the patient's vasculature. The guidewire 62 is advanced and steered into the vascular conduit 64 of interest and then poked through the lesion 66 requiring treatment. With the guidewire 62 in place, the balloon 14 is collapsed into the deflated configuration and the catheter 10 is threaded onto the guidewire 62 at an extracorporeal location. Next, the distal end of the catheter 10 is inserted into the access opening and advanced over the guidewire 62 until the balloon 14 is positioned in the vascular conduit 64 of interest and in front of the lesion 66 requiring treatment, as shown in FIG. 4.

Figure 5:
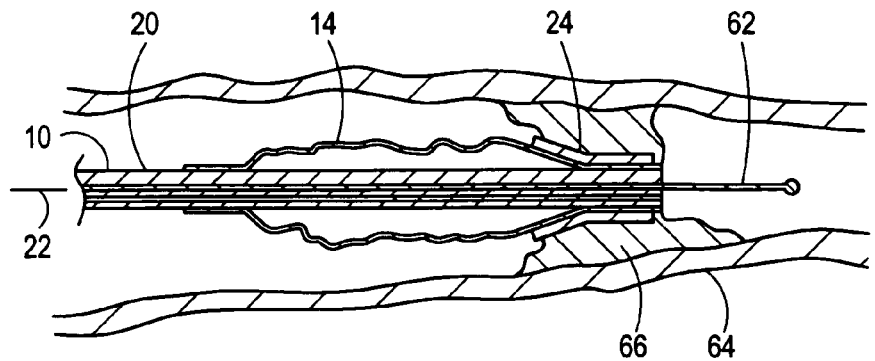
FIG. 5 is a sectional view as in FIG. 4 showing the distal portion of the catheter after the ribs have been wedged into the occluding lesion.

Next, as shown in FIG. 5, the catheter 10 is axially advanced to wedge the simulated tapered surface created by the ribs 24 into the lesion 66 and establish a passageway through the lesion 66 surrounding the guidewire 62. To drive the ribs 24 into the lesion 66 and create the required passageway, the distal end of the catheter 10 can be axially reciprocated back and forth from the periphery. Additionally, the balloon 14 can be partially inflated once the ribs 24 have been partially or totally embedded into the lesion 66 to assist in the creation of the passageway.

Figure 6:
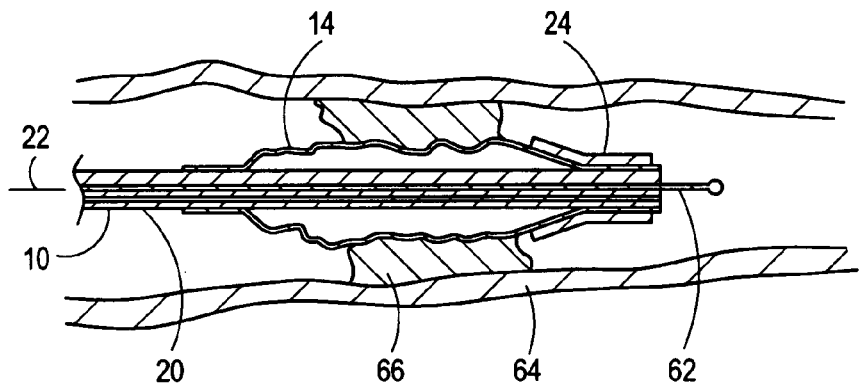
FIG. 6 is a sectional view as in FIG. 4 showing the distal portion of the catheter after the occluding lesion has been crossed and the dilatation balloon is in position to dilate the lesion.
Figure 7:
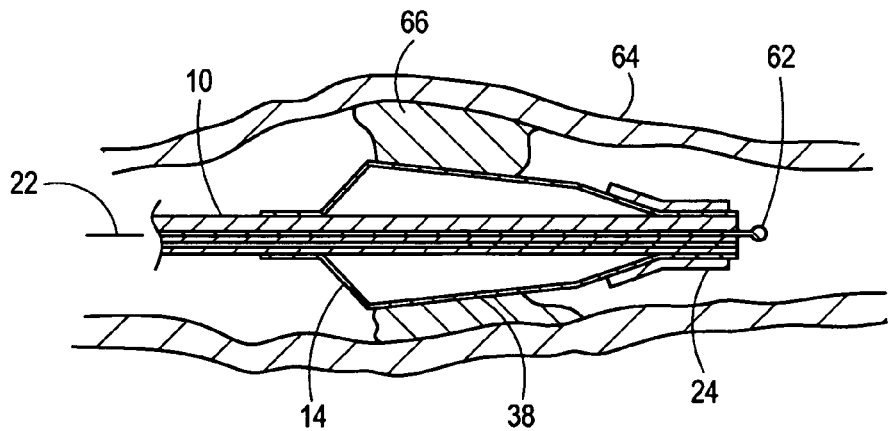
FIG. 7 is a sectional view as in FIG. 4 showing the distal portion of the catheter after inflation of the balloon to dilate the lesion.

FIG. 6 shows the position of the catheter 10 after the ribs 24 have crossed the lesion 66. As shown, once the ribs 24 have crossed the lesion 66, the working section 38 of the balloon 14 can be positioned to dilate the lesion 66. FIG. 7 shows the distal portion of the catheter 10 after the balloon 14 has been inflated to dilate the lesion 66 and restore blood flow to the affected vascular conduit 64. After the lesion 66 has been dilated, the balloon 14 can be deflated to thereby allow the catheter 10 to be moved to another treatment site or withdrawn from the patient's body.

While the particular apparatus and methods as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A catheter for dilating a lesion in a vascular conduit of a patient, said catheter comprising:
    an inner tube defining a longitudinal axis;
    an inflatable balloon mounted on said inner tube, said balloon extending from a proximal end to a distal end; and
    a dilatation unit having a plurality of ribs with each said rib extending from a first end to a second end and wherein said first end is distanced from said longitudinal axis at a radial distance $d_1$ and said second end distanced from said longitudinal axis at a radial distance $d_2$ with $d_1<d_2$, wherein each said rib comprises a first elongated portion aligned substantially parallel with said longitudinal axis and a second elongated portion extending from said first portion and at an angle, $\alpha$, thereto.

2. A catheter as recited in claim 1 wherein said angle, $\alpha$, is between approximately fifteen degrees and forty-five degrees (15°-45°).

3. A catheter as recited in claim 1 wherein each said rib is made of a material selected from the group of materials consisting of Liquid Crystal Polymer, Polyphenylene Sulfide and Polyethylene Naphthalate.

4. A catheter as recited in claim 1 wherein said dilatation unit has at least six said ribs.

5. A catheter as recited in claim 1 wherein said balloon is formed with a cylindrically shaped distal section with said first end of each said rib attached to said distal section and said second end of each said rib attached to said balloon proximal said distal section.

6. A catheter as recited in claim 5 wherein said balloon is further formed with a working section for contacting the lesion during dilation and a distal transition section connecting said working section to said distal section and wherein said second end of said rib is attached to said distal transition section.

* * * * *